United States Patent [19]

Haydock et al.

[11] 4,087,554

[45] May 2, 1978

[54] METHOD FOR IMPROVING GROWTH RATE AND FEED EFFICIENCY

[75] Inventors: David Bryan Haydock; Michael James Smithers, both of Macclesfield, England

[73] Assignee: Imperial Chemical Industries Limited, London, England

[21] Appl. No.: 622,159

[22] Filed: Oct. 14, 1975

[30] Foreign Application Priority Data

Oct. 30, 1974 United Kingdom ............... 46967/74
May 5, 1975 United Kingdom ............... 18713/75

[51] Int. Cl.$^2$ .................. A61K 31/03; A61K 31/085; A61K 31/19
[52] U.S. Cl. ............................... 424/353; 260/612 R; 260/613 R; 260/645; 260/646; 260/649 F; 260/649 R; 424/317; 424/324; 424/339; 424/340; 424/346; 424/347; 424/348; 424/349; 568/707; 568/717; 568/721; 568/745; 568/744

[58] Field of Search ............... 424/353, 349, 346, 347, 424/348, 346, 339, 317, 319, 324

[56] References Cited

U.S. PATENT DOCUMENTS

| 3,862,333 | 1/1975 | Chalupa et al. | 424/353 |
| 3,885,036 | 5/1975 | Moyle | 424/275 |

OTHER PUBLICATIONS

Wallace, J. of Animal Science, vol. 31, Jul.–Dec., 1970), pp. 1118 to 1125.

*Primary Examiner*—Sam Rosen
*Attorney, Agent, or Firm*—Cushman, Darby & Cushman

[57] ABSTRACT

The disclosure relates to a method for use in the practice of animal husbandry which comprises the oral administration to non-ruminant animals of an iodonium salt. Solid or liquid compositions of said iodonium salts for use in the said method are also disclosed. Certain of the iodonium sats used in the said method are novel compounds.

5 Claims, No Drawings

METHOD FOR IMPROVING GROWTH RATE AND FEED EFFICIENCY

This invention relates to methods, compositions and chemical compounds for use in animal husbandry for improving the growth of non-ruminant animals, for improving the efficiency of the utilisation of animal foodstuffs, and for reducing the incidence of scouring.

It is known, for example from German Offenlegungsschrift No. 2,413,222, that certain diaryl iodonium salts of the formula $R_2I^+.Z^-$, wherein the two Rs, which may be the same or different, are phenyl, naphthyl, furyl, thienyl or pyridyl optionally substituted by one or more trivial substituents known to the art and $Z^-$ is an inorganic or organic anion derived from a non-toxic, pharmaceutically acceptable acid, are useful in the husbandry or ruminant animals, such as sheep and cattle. The administration to such ruminant animals of an oral composition containing as an active ingredient a diaryliodonium salt as defined above is said to be useful for inhibiting the microbial deamination of amino acids and protein in the rumen, thereby allowing the amino acid units to pass through the destructive melieu of the rumen and to be absorbed in the lower gut. The amino acids and protein are thus made available for useful processes in the animal, instead of being lost in the form of useless ammonia, which is converted to urea. The consequences of such use of a diaryl iodonium salt for the inhibition of microbial deamination in ruminants are, therefore, increased productivity, daily weight gain and feed efficiency in growing and fattening cattle and feeder lambs, and improving wool production in mature lambs and sheep.

The process of microbial protein degradation is well known to be of little significance in the nutrition of non-ruminant animals, and it could not be expected that a diaryl iodonium salt which inhibits microbial deamination in the rumen of ruminant animals could have any improving effect on daily live weight gain or feed efficiency in non-ruminant animals, in which the process of ruminal microbial deamination cannot occur. It is extremely surprising, therefore, that we have now discovered, and herein lies our invention, that similar diaryl iodonium salts are useful in the husbandry of non-ruminant animals for producing an increase in growth rate and feed efficiency, and we have also discovered that the administration of such compounds reduces the incidence of scouring, particularly in young pigs.

According to the invention, therefore, there is provided a method for use in the practice of animal husbandry which comprises orally administering to meat-producing, non-ruminant animals, for example chickens, turkeys, ducks, geese, pigs, lambs and milk-fed calves (which do not have a functional rumen) and rabbits, an iodonium salt of the formula $R^1R^2I^+.X^-$ wherein $R^1$ and $R^2$, which may be the same or different, are each a phenyl, naphthyl or thienyl radical optionally bearing one or more substituents selected from nitro, hydroxy and carboxy radicals, halogen atoms, alkyl, alkoxy and alkanoylamino radicals each of up to 6 carbon atoms, cycloalkyl radicals of 3 to 7 carbon atoms, and phenyliodonio and thienyliodonio radicals optionally bearing one or more substituents as defined above, and $X^-$ is a physiologically acceptable anion.

Preferred values for $R^1$ and $R^2$ are phenyl and thienyl radicals optionally substituted as defined above, and a preferred value for $R^1$ and/or $R^2$ when either is a thienyl radical, is a 2-thienyl radical optionally substituted.

A suitable value for an optional substituent in $R^1$ or $R^2$ which is a halogen atom is, for example, a chlorine, bromine, iodine or fluorine atom; a suitable value for an optional substituent in $R^1$ or $R^2$ which is an alkyl, alkoxy or alkanoylamino radical of up to 6 carbon atoms is, for example, a methyl, ethyl, n-propyl, isopropyl, n-butyl, s-butyl, t-butyl, pentyl, hexyl, methoxy, ethoxy, n-propxy, isopropoxy, n-butoxy, s-butoxy, t-butoxy, pentyloxy, hexyloxy, acetamido, propionamido or butyramido radical; and a suitable value for an optional substituent in $R^1$ or $R^2$ which is a cycloalkyl radical of 3 to 7 carbon atoms is, for example, a cyclopentyl or cyclohexyl radical.

A suitable value for the physiologically-acceptable anion $X^-$ is, for example, a chloride, bromide, iodide, hydrogen sulphate, sulphate, nitrate, phosphate, toluene-p-sulphonate, acetate, trifluoroacetate, hydrogen succinate, succinate, hydrogen tartrate, tartrate, citrate, or maleate.

A preferred group of iodonium salts which may be used in the method of the invention comprises those compounds wherein either $R^3$ or $R^4$ is a 4-chlorophenyl or 4-fluorophenyl radical.

Particular preferred iodonium salts which may be used in the method of the invention are bis(4-chlorophenyl)-, bis(4-fluorophenyl)-, di(2-thienyl)-, phenyl(2-thienyl)-, (4-chlorophenyl)(4-tolyl)-, bis(4-chloro-2,5-dimethylphenyl)-, (4-chlorophenyl)(4-fluorophenyl)-, (4-chlorophenyl)(2,4,5-trimethylphenyl)-, (4-fluorophenyl)phenyl-, (4-chloro-2,5-dimethylphenyl)phenyl-, (4-chlorophenyl)(4-methoxyphenyl)- and (4-fluorophenyl)(4-tolyl)iodonium salts, especially the chlorides and bromides.

In the method of the invention, the iodonium salt is preferably orally administered to the animals as a supplement to their diet, that is to say in admixture with solid food, dissolved in the drinking water, or, for young animals such as pigs or calves, dissolved in whole milk or skim milk. It is generally convenient to administer the iodonium salt mixed with the animals' normal nutritionally balanced diet, in the form of a supplemented foodstuff containing from 0.0001% w/w (1 g. per metric ton) to 0.025% w/w (250 g. per metric ton) of an iodonium salt as defined above, or from 0.0001% w/w (1 g. per metric ton) to 0.005% w/w (50 g. per metric ton) of a preferred iodonium salt. The animals may be fed with such a supplemented foodstuff for substantially the whole of their growing period, or for only a part of their growing period, preferably the early part and/or the period leading up to slaughter. The increase in growth rate achieved by the practice of the method of the invention enables animals to be brought to market weight, or slaughtering weight, in a shorter growing period than normal, or it enables heavier animals to be produced at the end of the normal growing period. The practice of the method of the invention also achieves economic benefit for the farmer and the agricultural industry in that a given weight gain in the animals is achieved using less food than normal by reason of the increase in feed efficiency achieved by the method.

According to a further feature of the invention there is provided an animal foodstuff composition for use in the method of the invention, which comprises an iodonium salt as defined above, together with a liquid or solid, edible non-toxic diluent or carrier.

A suitable liquid diluent or carrier is, for example, drinking water, whole milk or skim milk. A suitable solid, edible non-toxic diluent or carrier may be, for example, a nutritionally balanced animal foodstuff, for example a standard broiler chicken diet of ground grain and grain by-products, animal protein supplemented by vitamins and minerals, a standard commercial pig fattening or finishing diet or other conventional animal foodstuff, or it may be an inert, solid diluent or carrier of little or no nutritional value, for example kaolin, talc, calcium carbonate, fuller's earth, attapulgus clay, ground oyster shells, ground limestone, starch or lactose.

The animal foodstuff composition of the invention may take the form of a supplemented foodstuff for direct feeding to animals, in which case it will contain from 0.0001% w/w to 0.025% w/w of an iodonium salt, preferably 0.0001% w/w to 0.005% w/w of a preferred iodonium salt, in admixture with a conventional nutritionally balanced animal foodstuff, or it may take the form of a concentrated premix for dilution with a conventional foodstuff to produce a supplemented foodstuff suitable for direct feeding, and such a premix will contain from 0.025% w/w to 50% w/w of an iodonium salt, in admixture with either a nutritionally balanced animal foodstuff or an inert solid diluent such as ground limestone. Such a premix may be diluted in conventional manner, preferably in two or more steps to ensure even mixing, with a conventional animal foodstuff to give a supplemented foodstuff suitable for direct feeding to animals in the method of the invention.

At optimum growth promoting inclusion levels, no indications of any toxic effect are observed.

A preferred group of iodonium salts, and particular preferred iodonium salts which may be used in the compositions of the invention are those defined above.

According to a further feature of the invention there is provided a process for the manufacture of a solid animal foodstuff composition as defined above which comprises evenly dispersing an iodonium salt, as defined above in a solid edible, non-toxic diluent or carrier.

Certain of the iodonium salts defined above are novel, and thus, according to a further feature of the invention there is provided a novel, iodonium salt of the formula $R^3R^4I^+.X^-$ wherein: either $R^3$ is a 2-thienyl radical, optionally substituted as defined above and $R^4$ is a 2-thienyl radical substituted as defined above, a phenyl radical bearing three or more substituents as defined above or a naphthyl radical optionally substituted as defined above; or $R^3$ is a 2-thienyl radical substituted as defined above and $R^4$ is a phenyl or naphthyl radical optionally substituted as defined above; or $R^3$ is a 3-thienyl radical optionally substituted as defined above and $R^4$ is a phenyl, naphthyl or thienyl radical optionally substituted as defined above; or $R^3$ is an unsubstituted phenyl radical and $R^4$ is a 4-methylthien-2-yl, 5-chlorothien-2-yl, 5-methylthien-2-yl, 5-nitrothien-2-yl, 4-cyclohexylphenyl or 4-chloro-2,5-dimethylphenyl radical; or $R^3$ is a 4-chlorophenyl radical and $R^4$ is a 4-methylthien-2-yl, 4-fluorophenyl, 4-tolyl 4-methoxy-3-nitrophenyl, 4-s-butylphenyl, 2,4-xylyl, mesityl, 2,3,4-trimethylphenyl, 4-bromophenyl, 2,4-dimethoxyphenyl, 4-chloro-2,5-dimethylphenyl, 4-acetamidophenyl or 4-(4-chlorophenyliodonio)phenyl radical; or $R^3$ is an unsubstituted 2-thienyl radical and $R^4$ is a 3-carboxyphenyl, 2-chlorophenyl, 3-nitrophenyl, 4-(2-thienyliodonio)phenyl or 3-(2-thienyliodonio)phenyl radical; or $R^3$ is a 4-fluorophenyl radical and $R^4$ is a 4-methylthien-2-yl, 4-tolyl or 3-nitrophenyl radical; or $R^3$ is a 4-tolyl radical and $R^4$ is a 4-cyclohexylphenyl radical; or $R^3$ is a 4-methoxyphenyl radical and $R^4$ is a 3-(4-methoxyphenyliodonio)phenyl radical; or $R^3$ and $R^4$ are each a 5-methylthien-2-yl, 5-bromothien-2-yl, 4-bromothien-2-yl, 4-methylthien-2-yl, 4-chloro-2,5-dimethylphenyl, 4-chloro-3-methylphenyl, 4-bromo-2,5-dimethylphenyl or 4-methoxy-3-nitrophenyl radical; and $X^-$ is a pharmaceutically acceptable anion.

Particular suitable substituents in $R^3$ and $R^4$ are those listed above in the definition of $R^1$ and $R^2$, and suitable anions $X^-$ are those defined above.

A preferred group of novel iodonium salts of the invention comprises those compounds wherein either $R^3$ or $R^4$ is a 4-chlorophenyl or 4-fluorophenyl radical.

Particular preferred novel iodonium salts of the invention are bis(4-methylthien-2-yl)-, (4-chlorophenyl)-(4-methylthien-2-yl)-, (4-methylthien-2-yl)phenyl, (4-fluorophenyl)(4-methylthien-2-yl)-, (4-fluorophenyl)(3-nitrophenyl)-, (4-chlorophenyl)(4-fluorophenyl)-, (4-chlorophenyl)(4-tolyl)-, (4-fluorophenyl)(4-tolyl)-, bis(4-chloro-2,5-dimethylphenyl)-, (4-chlorophenyl)(2,4-xylyl)-, (4-chlorophenyl)mesityl-, (4-chloro-2,5-dimethylphenyl)phenyl- and (4-acetamidophenyl)-(4-chlorophenyl)- iodonium salts, especially the chlorides and bromides.

The novel iodonium salts of the invention may be manufactured by processes known in themselves for the manufacture of chemically analogous compounds. Thus, according to a further feature of the invention, there is provided a process for the manufacture of an iodonium salt of the formula $R^3R^4I^+.X^-$ which comprises, for salts wherein $R^3$ and $R^4$ are the same, the reaction of a compound $R^3H$ with iodosyl sulphate, for example in sulphuric acid, with an alkali metal iodate, for example sodium or potassium iodate, in acetic anhydride and sulphuric acid, or with an iodine tri($C_{1-4}$ alkanoate), for example iodine triacetate or iodine tris(trifluoro-acetate), in the presence of an acid, or, for those compounds wherein $R^3$ and $R^4$ are the same or different, with a di($C_{1-4}$-alkanoyloxy)iodo compound of the formula $R^4I(OR^5)_2$ wherein $R^5$ is a $C_{1-4}$-alkanoyl radical of 1 to 4 carbon atoms, for example a diacetoxyiodo compound.

The invention is illustrated, but not limited, by the following Examples:

EXAMPLE 1

Premixes suitable for dilution with an animal foodstuff may be manufactured by incorporating 5,10,25,50 or 100 g. of bis(4-chlorophenyl)iodonium chloride in a standard broiler chicken diet comprising ground maize and fishmeal, with added lysine, methionine, vitamins and minerals so that the final weight of the premix is 500 g.

Other premixes may be manufactured by replacing the bis(4-chlorophenyl)iodonium chloride with a similar quantity of bis(4-fluorophenyl)iodonium chloride, di(2-thienyl)iodonium chloride or phenyl(2-thienyl)iodonium chloride, or with any other iodonium salt as hereinbefore described.

EXAMPLE 2

Premixes suitable for dilution with an animal foodstuff may be manufactured by the process described in Example 1, using ground limestone in place of the standard broiler chicken diet.

EXAMPLE 3

An animal foodstuff suitable for direct feeding to poultry may be manufactured by intimately mixing 500 g. of a premix, obtained as described in Example 1 or 2, with 4.5 kg. of standard broiler chicken diet, and then uniformly mixing the mixture so obtained with 995 kg. of standard broiler chicken diet to obtain a poultry foodstuff containing 5, 10, 25, 50 or 100 g. of an iodonium salt per metric ton, depending on the concentration of iodonium salt in the premix used.

to which the indicated weight in parts per million of an iodonium salt was added. At the end of the test period, the birds were weighed, and the liveweight gain for each pen was determined. Standard statistical procedures indicate a significant ($P<0.05$) growth promoting response for a test compound when the mean liveweight gain of treated birds was 30% or more greater than the mean liveweight gain of the control birds. The feed efficiency (feed consumed/liveweight gain) was also determined for each diet.

The following results were obtained with representative iodonium salts:

| $R^1$ | $R^2$ | X | p.p.m. of iodonium salt | % difference between increases in weights of treated and control groups | % difference between feed efficiencies of treated and control groups |
|---|---|---|---|---|---|
| 4-tolyl | 4-tolyl | Cl | 25 | 57 | 53 |
| 4-acetamidophenyl | 4-acetamidophenyl | I | 100 | 46 | 53 |
| 3-nitrophenyl | 3-nitrophenyl | Cl* | 50 | 55 | 41 |
|  |  | $HSO_4$ | 50 | 44 | 38 |
| 2-thienyl | 2-thienyl | Cl | 50 | 82 | 60 |
|  |  |  | 25 | 66 | 54 |
|  |  |  | 10 | 42 | 31 |
| 4-methoxyphenyl | 4-methoxyphenyl | Br | 50 | 78 | 67 |
| 4-methyl-2-thienyl | 4-methyl-2-thienyl | Br | 50 | 70 | 65 |
| 5-methyl-2-thienyl | 5-methyl-2-thienyl | Cl | 50 | 49 | 45 |
| 2,4-dichlorophenyl | 2,4-dichlorophenyl | Cl | 50 | 30 | 22 |
| 4-fluorophenyl | 4-fluorophenyl | Cl | 50 | 78 | 71 |
|  |  |  | 25 | 66 | 44 |
|  |  |  | 10 | 76 | 62 |
|  |  | Br | 50 | 64 | 51 |
|  |  | I | 50 | 42 | 42 |
| phenyl | 2-thienyl | Cl | 50 | 86 | 78 |
|  |  |  | 25 | 48 | 48 |
|  |  |  | 10 | 42 | 56 |
|  |  | $NO_3$ | 50 | 60 | 72 |
| 4-chlorophenyl | 4-chlorophenyl | Cl | 50 | 80 | 75 |
|  |  |  | 25 | 36 | 32 |
|  |  | $HSO_4$ | 100 | 54 | 53 |
|  |  | toluene-p-sulphonate | 25 | 39 | 48 |
| 1-naphthyl | 1-naphthyl | Br | 50 | 43 | 45 |
| 4-cyclohexylphenyl | 4-cyclohexylphenyl | Br | 25 | 47 | 43 |
| 4-chlorophenyl | 2-thienyl | Cl | 50 | 54 | 51 |
| 4-fluorophenyl | 2-thienyl | Cl | 50 | 55 | 55 |
| 4-bromophenyl | 4-bromophenyl | $HSO_4$ | 100 | 41 | 31 |
| 4-chlorophenyl | 4-methyl-2-thienyl | Cl | 50 | 65 | 54 |
| phenyl | 4-methyl-2-thienyl | Cl | 100 | 61 | 55 |
| phenyl | 5-chloro-2-thienyl | Cl | 50 | 34 | 31 |
| 4-fluorophenyl | 4-methyl-2-thienyl | Cl | 25 | 63 | 69 |
| phenyl | 5-methyl-2-thienyl | Cl | 50 | 43 | 40 |
| 4-nitrophenyl | 2-thienyl | Cl | 50 | 79 | 63 |
| 4-tolyl | 2-thienyl | Cl | 50 | 48 | 39 |
| 3-tolyl | 2-thienyl | Cl | 100 | 78 | 69 |
| 3-chlorophenyl | 2-thienyl | Cl | 100 | 49 | 41 |
| 3-carboxyphenyl | 2-thienyl | Cl | 25 | 41 | 38 |
| 2-chlorophenyl | 2-thienyl | Cl | 50 | 75 | 69 |
| 3-nitrophenyl | 2-thienyl | Cl | 50 | 55 | 51 |
| phenyl | 5-nitro-2-thienyl | Br* | 50 | 61 | 53 |
| 4-bromo-2-thienyl | 4-bromo-2-thienyl | Cl* | 50 | 43 | 44 |
| 5-bromo-2-thienyl | 5-bromo-2-thienyl | Cl | 100 | 31 | 19 |
| 3-nitrophenyl | 4-fluorophenyl | Cl* | 50 | 119 | 104 |
| phenyl | 4-iodophenyl | Cl* | 50 | 106 | 93 |
| 4-tolyl | 4-chlorophenyl | Cl* | 50 | 136 | 134 |
| 4-chlorophenyl | 2-chlorophenyl | Cl* | 50 | 51 | 42 |
| 4-chloro-3-methylphenyl | 4-chloro-3-methylphenyl | Cl* | 50 | 61 | 60 |
| 4-chloro-2,5-dimethylphenyl | 4-chloro-2,5-dimethylphenyl | Cl* | 50 | 131 | 110 |
| 4-chlorophenyl | 4-fluorophenyl | Cl* | 50 | 145 | 138 |
| 4-hydroxyphenyl | 2-thienyl | Cl* | 50 | 205 | 185 |
| 4-fluorophenyl | 4-tolyl | Cl* | 50 | 131 | 114 |

*Compounds identified thus were tested for 6 days, all other compounds for 3 days.

EXAMPLE 4

Groups of 20 1-day old chickens were weighed, and placed in small floor pens, bedded with wood shavings and provided with automatic water fountains. The birds in 16 randomly chosen such pens were fed for 3 or 6 days on a nutritionally balanced control diet containing no known growth promoter, and the birds in four other pens were fed for the same period on the same basal diet

EXAMPLE 5

One hundred and three young pigs, initial weight approximately 15 kg. were weighed and divided into four matched experimental groups of 25 or 26 animals each. The pigs were fed individually twice a day, and were given the quantity of food they could just eat in 20 minutes. One group was fed on a standard basal diet containing no known growth promoter, a second group was fed on the same diet with 50 g. per metric ton of bis(4-fluorophenyl)iodonium chloride added, a third group was fed on the basal diet with 25 g. per metric ton of bis(4-fluorophenyl)iodonium chloride added, and the fourth group was fed on the basal diet with 10 g. per metric ton of nitrovin, a known growth promoter added. After 28 days, the animals were weighed and the mean daily liveweight gain and food conversion ratio (kg. food per kg. weight gain) were determined.

The following results were obtained:

| Diet | No. of pigs | Mean daily liveweight gain | | Food conversion ratio | |
|---|---|---|---|---|---|
| | | kg. | Standard error | kg. food/ kg. gain | Standard error |
| 1 | 25 | 0.258 | 0.009 | 3.46 | 0.06 |
| 2 | 26 | 0.286* | 0.007 | 3.15** | 0.05 |
| 3 | 26 | 0.266 | 0.010 | 3.24* | 0.04 |
| 4 | 26 | 0.248 | 0.008 | 3.29 | 0.08 |

*significant at P 0.05 level
**significant at P 0.01 level

EXAMPLE 6

The procedure described in Example 5 was repeated using four groups, each of 20 pigs, fed respectively with (1) basal diet, (2) basal diet plus 50 g. per metric ton of bis(4-chlorophenyl)iodonium chloride, (3) basal diet plus 25 g. per metric ton of bis(4-chlorophenyl)iodonium chloride and (4) basal diet plus 10 g. per metric ton of nitrovin, a known growth promoter. The results were determined after 23 days and after 63 days were as follows:

| Diet | Mean daily liveweight gain | | Food conversion ratio | |
|---|---|---|---|---|
| | kg. | Standard error | kg. food/ kg. gain | Standard error |
| 23 days | | | | |
| 1 | 0.705 | 0.016 | 2.582 | 0.035 |
| 2 | 0.751* | 0.014 | 2.507* | 0.035 |
| 3 | 0.730 | 0.016 | 2.537 | 0.034 |
| 4 | 0.722 | 0.017 | 2.584 | 0.037 |
| 63 days | | | | |
| 1 | 0.764 | 0.009 | 3.068 | 0.047 |
| 2 | 0.804* | 0.011 | 2.959* | 0.036 |
| 3 | 0.801* | 0.014 | 2.960* | 0.040 |
| 4 | 0.787 | 0.008 | 2.966* | 0.044 |

*significant at P<0.05 level

EXAMPLE 7

The experiment described in Example 4 was repeated, using 6 pens each of 30 cockerels for each of the specified diets, and assessing the weight gain and feed conversion ratios after a 4-week trial period. The following results were obtained in two separate experiments:

Experiment 1

| Diet | Mean liveweight (g) | Feed Conversion ratio |
|---|---|---|
| Basal | 216.8 | 2.17 |
| Basal + nitrovin 10 ppm | 246.2** | 1.99* |
| Basal + bis(4-fluorophenyl)iodonium chloride 50 ppm | 220.8 | 2.17 |
| Basal + bis(4-fluorophenyl)iodonium chloride 25 ppm | 251.7*** | 2.09 |
| Basal + di-(2-thienyl)iodonium chloride 50 ppm | 239.2** | 2.10 |
| Basal + di-(2-thienyl)iodonium chloride 25 ppm | 228.3* | 2.18 |
| Basal + phenyl(2-thienyl)iodonium chloride 50 ppm | 248.0** | 2.13 |
| Basal + phenyl(2-thienyl)iodonium chloride 25 ppm | 235.8* | 2.11 |
| Basal + bis(4-chlorophenyl)iodonium chloride 50 ppm | 236.3* | 2.12 |
| Basal + bis(4-chlorophenyl)iodonium chloride 25 ppm | 230.2* | 2.13 |

*Significantly different from control (basal) at p < 0.05 level
**Significantly different from control (basal) at p < 0.01 level
***Significantly different from control (basal) at p < 0.001 level Experiment 2

| Diet | | Mean liveweight (g) | Feed conversion ratio |
|---|---|---|---|
| Basal | | 253.2 | 2.06 |
| Basal + nitrovin | 10 ppm | 282.1*** | 1.86 |
| Basal + bis(4-chlorophenyl)iodonium chloride | 100 ppm | 273.3* | 1.98 |
| " | 50 ppm | 269.3* | 1.95 |
| " | 25 ppm | 263.5 | 1.96 |
| Basal + bis(4-fluorophenyl)iodonium chloride | 50 ppm | 273.1* | 1.93 |
| " | 25 ppm | 265.1 | 2.02 |

Significances as in Experiment 1 above.

EXAMPLE 8

A solution of 4-(diacetoxyiodo)fluorobenzene (5.3 g.) in acetic anhydride (16 ml.) and trifluoroacetic acid (4.7 ml.) was stirred and cooled to −20° C., and a solution of 3-methylthiophen (3.5 ml.) in acetic anhydride (19 ml.) was added dropwise. After the completion of the addition, the reaction mixture was maintained below −10° C. for ½ hour and stored at 4° C. overnight. The solvents were evaporated under reduced pressure and the residue was dissolved in boiling water (75 ml.) to give a solution which was treated with carbon and filtered. Aqueous ammonium chloride added to the filtrate precipitated (4-fluorophenyl)(4-methylthien-2-yl)iodonium chloride which was filtered off, washed well with, successively, water, ethanol and ether, and dried, m.p. 218° C.

In a similar manner, using the appropriately substituted diacetoxyiodobenzene and the appropriately substituted thiophen as the starting materials, the following compounds were obtained:

$R^3R^4I.^+X^-$

| $R^3$ | $R^4$ | X | m.p.(° C.) |
|---|---|---|---|
| 4-chlorophenyl | 4-methylthien-2-yl | Cl | 272–273 |
| phenyl | 4-methylthien-2-yl | Cl | 255 (decomp.) |
| phenyl | 5-chlorothien-2-yl | Cl | 182 (decomp.) |
| phenyl | 5-methylthien-2-yl | Cl | 188 (decomp.) |
| 3-carboxyphenyl | 2-thienyl | Cl | 225 |
| 2-chlorophenyl | 2-thienyl | Cl | 249 (decomp.) |
| 3-nitrophenyl | 2-thienyl | Cl | 209 (decomp.) |

-continued

R³R⁴I.⁺X⁻

| R³ | R⁴ | X | m.p.(° C.) |
|---|---|---|---|
| phenyl | 5-nitrothien-2-yl | Br* | 194 (decomp.) |

*Potassium bromide used instead of ammonium chloride to form the salt.

EXAMPLE 9

Fuming nitric acid (1.75 ml.) was added dropwise to stirred acetic anhydride (5.5 ml.) cooled to −20° C., followed by iodine (1.7 g.) and trifluoroacetic acid. The mixture was allowed to warm to room temperature and was stirred until the iodine dissolved completely. The solvents were evaporated under reduced pressure below 40° C., and the residue of crude iodine tris(trifluoroacetate) was treated at room temperature with acetic anhydride (11 ml.). The resulting solution was stirred and cooled to −10° C. and a solution of 2-methylthiophen (5.0 g.) in acetic anhydride (23 ml.) and trifluoroacetic acid (3.2 ml.) was added dropwise during 1 hour. The reaction mixture was stored at 4° C. for 16 hours, and the solvents were evaporated under reduced pressure. The residue was dissolved in boiling water (75 ml.), and the solution was treated with charcoal and filtered. Addition of aqueous ammonium chloride to the cooled filtrate precipitated bis(5-methylthien-2-yl)iodonium chloride, which was filtered off and dried, m.p. 259° C. with decomposition.

In a similar manner, using the appropriately substituted thiophens, there were obtained the following compounds:

bis(5-bromothien-2-yl)iodonium chloride, m.p. 168°–170° C. with decomposition;
bis(4-bromothien-2-yl)iodonium chloride, m.p. 175°–177° C. with decomposition;
bis(4-methylthien-2-yl)iodonium chloride, m.p. 250° C. with decomposition.

EXAMPLE 10

A mixture of 4-chloro(diacetoxyiodo)benzene (3.56 g.), fluorobenzene (3.84 g.) and acetic anhydride (30 ml.) was stirred and cooled to −20° C., then concentrated sulphuric acid (5.0 ml.) was added dropwise. The mixture was stirred below −10° C. for 1 hour, allowed to warm to room temperature and left overnight. The reaction mixture was cooled in an ice bath, and water (30 ml.) was added, keeping the temperature below 20° C. The solution was extracted with ether (5 × 20 ml.) and the extracts were discarded, and the aqueous phase was treated with aqueous ammonium chloride solution or hydrochloric acid. The (4-chlorophenyl)(4-fluorophenyl)iodonium chloride which was precipitated was filtered off, washed well with water and dried in vacuo, m.p. 207° C. with decomposition.

In a similar manner, starting with the appropriately substituted diacetoxyiodobenzene and the appropriate halogenobenzene, the following compounds were obtained:

(4-chlorophenyl)(4-tolyl)iodonium chloride, m.p. 169° C. with decomposition;
(4-fluorophenyl)(4-tolyl)iodonium chloride, m.p. 226° C. with decomposition;
(4-fluorophenyl)(3-nitrophenyl)iodonium chloride, m.p. 238° C. with decomposition;

EXAMPLE 11

A mixture of 2-chloro-p-xylene (14 ml.), potassium iodate (10.7 g.) and acetic anhydride (20 ml.) was stirred and cooled below 5° C. while a cold solution of concentrated sulphuric acid (7.5 ml.) and acetic anhydride (14.7 ml.) was added over 2½ hours. The reaction mixture was then stirred at 4° C. for 1 hour and at room temperature for 72 hours, then was cooled to 4° C. and kept below 10° C. while water (50 ml.) was added dropwise over ½ hour, followed by ether (50 ml.). The aqueous phase was separated, washed with ether (2 × 50 ml.), filtered, and stirred and cooled in ice while concentrated hydrochloric acid (5 ml.) was added dropwise. The precipitated bis(4-chloro-2,5-dimethylphenyl)iodonium chloride was filtered off, washed with water and dried in vacuo, m.p. 166°–168° C.

In a similar manner, using 2-chlorotoluene, there was obtained a mixture of isomeric bis(chlorotolyl)iodonium chlorides, m.p. 200°–203° C.

EXAMPLE 12

The procedure described in Example 4 was repeated, with the compounds shown in the following table being administered at 50 p.p.m. for 6 days, to give the results displayed below:

| R¹ | R² | X | % difference between increases in weights of treated and control groups | % difference between feed efficiencies of treated and control groups |
|---|---|---|---|---|
| 4-bromo-2,5-dimethylphenyl | 4-bromo-2,5-dimethylphenyl | Cl | 84 | 97 |
| 4-methoxy-3-nitrophenyl | 4-methoxy-3-nitrophenyl | Cl | 129 | 108 |
|  |  | HSO₄ | 96 | 82 |
| phenyl | mesityl | Br | 72 | 56 |
| 4-chlorophenyl | 4-methoxy-3-nitrophenyl | Cl | 125 | 106 |
| 4-chlorophenyl | 4-s-butylphenyl | Cl | 129 | 117 |
| 4-chlorophenyl | 2,4-xylyl | Br | 223 | 200 |
| 4-chlorophenyl | phenyl | Br | 212 | 185 |
| 4-fluorophenyl | phenyl | Br | 214 | 190 |
| 4-chlorophenyl | mesityl | Br | 260 | 230 |
| 4-chlorophenyl | 2,3,4-trimethylphenyl | Br | 190 | 175 |
| 3,4-dichlorophenyl | phenyl | Cl | 91 | 91 |
| 4-chlorophenyl | 4-bromophenyl | Cl | 90 | 92 |
| 4-cyclohexylphenyl | phenyl | Br | 115 | 103 |
| 4-chlorophenyl | 2,4-dimethoxyphenyl | Br | 89 | 88 |
| 2,4,6-trichlorophenyl | phenyl | Cl | 65 | 77 |

EXAMPLE 13

Groups of 20 randomised 1-day old chickens were placed in small floor pens, bedded with wood shavings and provided with automatic water fountains. The birds in 16 randomly chosen such pens were fed for 6 days on a nutritionally balanced control diet containing no known growth promoter, and for each test compound the birds in four other pens were fed for the same period on the same basal diet to which the indicated weight in parts per million of an iodonium compound was added. At the end of the test period, the birds were weighed, and the total liveweight for each pen was determined, and the average value for the pens allocated to each diet was calculated. The following results were obtained. The "weight difference" is the difference between the weight of a treated group (A) and the weight of an untreated control group (B) expressed as a percentage of the weight of the untreated control group, that is:

$$\frac{A-B}{B} \times 100$$

| $R^1$ | $R^2$ | X | Weight difference % |
|---|---|---|---|
| 4-iodophenyl | phenyl | Br | 10.8 |
| " | " | Cl | 10.9 |
| 2-thienyl | 4-phenoxyphenyl | Cl | 7.5 |
| 4-phenoxyphenyl | 4-phenoxyphenyl | Cl | 10.4 |
| 4-chlorophenyl | 4-chloro-2,5-dimethyl-phenyl | Cl | 6.2 |
| 4-tolyl | 4-cyclohexylphenyl | Br | 4.6 |
| phenyl | 4-chloro-2,5-dimethyl-phenyl | Cl | 10.6 |
| 4-chlorophenyl | 4-methoxyphenyl | Cl | 12.6 |
| phenyl | 4-acetamidophenyl | Br | 7.0 |
| phenyl | 4-bromophenyl | Cl | 7.3 |
| " | " | Br | 3.5 |
| 4-chlorophenyl | 4-(4-chlorophenyl-iodonio)phenyl | 2Cl | 6.0 |
| 2-thienyl | 4-(2-thienyliodonio)-phenyl | 2 . CF$_3$CO$_2$ | 5.3 |
| 4-chlorophenyl | 4-acetamidophenyl | Cl | 9.3 |
| 4-methoxyphenyl | 3-(4-methoxyphenyl-iodonio)phenyl | 2Cl | 6.6 |
| 2-thienyl | 3-(2-thienyliodonio)phenyl | 2Cl | 2.9 |

EXAMPLE 14

The process described in Example 10 was repeated, using an appropriate diacetoxyiodobenzene and an appropriate halogenobenzene, to give the following iodonium salts:

(4-chlorophenyl)-4-methoxy-3-nitrophenyl)iodonium chloride, m.p. 219°–220° C.

(4-chlorophenyl)-(4-s-butylphenyl)iodonium chloride, m.p. 197°–198° C.

(4-chlorophenyl)-(2,4-xylyl)iodonium bromide, m.p. 164°–165° C.

(4-chlorophenyl)-mesityliodonium bromide, m.p. 150°–151° C.

(4-chlorophenyl)-2,3,4-trimethylphenyl)iodonium bromide, m.p. 192°–194° C.

[In this case, the addition of ether and water in the work-up procedure precipitated the bisulphate salt, which was isolated, dissolved in hot 50% aqueous acetic acid, and treated with aqueous potassium bromide to produce the iodonium bromide salt].

(3,4-dichlorophenyl)-phenyliodonium chloride, m.p. 180°–184° C. with decomposition.

(4-bromophenyl)-(4-chlorophenyl)iodonium chloride, m.p. 205°–206° C.

(4-cyclohexylphenyl)-phenyliodonium bromide, m.p. 201°–202° C.

(4-chlorophenyl)-(2,4-dimethoxyphenyl)iodonium bromide, m.p. 156°–158° C.

[In this case, trifluoroacetic acid was used in place of sulphuric acid.]

(4-chloro-2,5-dimethylphenyl)-(4-chlorophenyl)iodonium chloride, m.p. 171°–173° C.

(4-cyclohexylphenyl)-(4-toyl)iodonium bromide, m.p. 164°–165° C.

(4-chloro-2,5-dimethylphenyl)-phenyliodonium chloride, m.p. 193°–194° C.

(4-acetamidophenyl)-(4-chlorophenyl)iodonium chloride, m.p. 221°–222° C. with decomposition.

[In this case, a large excess of sulphuric acid was used.]

EXAMPLE 15

The process described in Example 11 was repeated, using an appropriate halogenobenzene in place of 2-chloro-p-xylene, to give bis(4-methoxy-3-nitrophenyl)iodonium chloride, m.p. 240°–241° C. with decomposition, [In this case, the addition of ether and water in the work-up procedure precipitated the bisulphate salt, m.p. 198°–202° C. with decomposition, which was converted to the chloride with hydrochloric acid] and bis(4-bromo-2,5-dimethylphenyl)-iodonium chloride, m.p. 167°–168° C.

EXAMPLE 16

A mixture of 1,4-bis(diacetoxyiodo)benzene (2.83 g.), acetic anhydride (25 ml.) and trifluoroacetic acid (6 ml.) was stirred and cooled to −5° C. while a cold solution of thiophen (3.95 ml.) in acetic anhydride (10 ml.) was added over 30 minutes. The mixture was stirred for 2 hours at −5° and 16 hours at room temperature. The solvents were removed in vacuo, the residue was dissolved in hot water, the solution was decolourised with charcoal and filtered, and on standing p-phenylene-bis(-thien-2-yl-iodonium)-bis(trifluoroacetate) crystallised from the filtrate. The solid was filtered off, washed with water then ether and dried in vacuo, m.p. 236°–238° C. (decomposition).

In a similar manner, using 1,3-bis-(diacetoxyiodo)benzene and either anisole or thiophen, and by adding hydrochloric acid to the aqueous solution of the trifluoroacetate salt, there were obtained respectively m-phenylene bis(4:methoxyphenyliodonium)dihydrochloride, m.p. 224°–226° C. and m-phenylene bis(2-thienyliodonium)dihydrochloride, m.p. 200° C. (decomposition).

EXAMPLE 17

A mixture of 1,4-bis(diacetoxyiodo)benzene (2.83 g.), acetic anhydride 30 ml. and chlorobenzene (5.10 ml.) was stirred and cooled to −15° C. while concentrated sulphuric acid (5 ml.) was added over 30 minutes. The mixture was stirred for 2 hours at 4° C., and 16 hours at room temperature. The reaction mixture was cooled in an ice bath and water (30 ml.) added, keeping the temperature below 20° C. The mixture was extracted with ether (4 × 20 ml.) and the stirred and cooled aqueous phase was treated with concentrated hydrochloric acid (2 ml. The p-phenylene-bis(4-chlorophenyliodonium)-dihydrochloride which was precipitated was filtered off, washed with water and ether, and dried in vacuo, m.p. 233°–235° C. (decomposition).

EXAMPLE 18

Seventy-two pigs, each initially weighing 30–35 kg., were allocated on the basis of sex and liveweight to eight matched groups of 9 pigs each. Each group was randomly assigned to one of eight diets, as specified in the Table below. All animals were fed individually twice daily on an accurately weighed quantity of the diet, according to a feeding scale which was related to body weight and was adjusted weekly. The trial was terminated after 48 days, and the mean liveweight gain and food conversion ratio (expressed as in Example 5 above) were determined for each group. The following results were obtained:

| Dietary supplement | | | | |
|---|---|---|---|---|
| Bis(4-chlorophenyl) iodonium chloride, 50 g./ton | Nitrovin 10 g./ton | copper 100 g./ton | Mean daily liveweight gain (g) | Food conversion ratio |
| − | − | − | 684 | 2.652 |
| + | − | − | 720 | 2.590 |
| − | + | − | 712 | 2.621 |
| + | + | − | 737 | 2.587 |
| − | − | + | 716 | 2.566 |
| + | − | + | 743 | 2.544 |
| − | + | + | 715 | 2.673 |
| + | + | + | 755 | 2.495 |

What we claim is:

1. A method for increasing the growth rate and feed efficiency of meat-producing non-ruminant animals which comprises orally administering to said meat-producing, non-ruminant animals, an effective amount of an iodonium salt of the formula $R^1R^2I^+ \cdot X^-$ wherein $R^1$ and $R^2$ which may be the same or different, are each phenyl or phenyl bearing one or more substituents selected from nitro, hydroxy, carboxy, halogen, alkyl, alkoxy and alkanoylamino each of up to 6 carbon atoms, cycloalkyl of 3 to 7 carbon atoms, and $X^-$ is physiologically acceptable anion.

2. The method of claim 1 wherein in the iodonium salt, $R^1$ and $R^2$, which may be the same or different, are each phenyl or phenyl bearing one or more substituents selected from nitro, hydroxy and carboxy chlorine, bromine, iodine, fluorine, methyl, ethyl,n-propyl, isopropyl, n-butyl, s-butyl, t-butyl, pentyl, hexyl, methoxy,ethoxy, n-propoxy, isopropoxy, n-butoxy, s-butoxy, t-butoxy, pentyloxy, hexyloxy, acetamido, propionamido, butyramido, cyclopentyl and cyclohexyl, and $X^-$ is a chloride, bromide, iodide, hydrogen sulphate, sulphate, nitrate, phosphate, toluene-p-sulphonate, acetate, trifluoroacetate, hydrogen succinate, succinate, hydrogen tartrate, tartrate, citrate or maleate anion.

3. The method of claim 1 wherein the iodonium salt is a bis(4-chlorophenyl)-, bis(4-fluorophenyl)-, (4-chlorophenyl) (4-tolyl)-, bis(4-chloro-2,5-dimethylphenyl)-, (4-chlorophenyl) (4-fluorophenyl)-, (4-chlorophenyl) (2,4,5-trimethylphenyl)-, (4-fluorophenyl)phenyl-, (4-chloro-2,5-dimethylphenyl)phenyl-, (4-chlorophenyl) (4-methoxyphenyl)- or (4-fluorophenyl)- (4-tolyl)-iodonium salt.

4. The method of claim 1 wherein the iodonium salt is administered, mixed with the animals' normal nutritionally balanced diet, in the form of a supplemented foodstuff containing from 0.0001% w/w to 0.025% w/w of the iodonium salt.

5. The method of claim 1 wherein said salt is (4-chlorophenyl) (4-fluorophenyl)iodonium chloride.

* * * * *